US011857653B2

United States Patent
Queiroz et al.

(10) Patent No.: US 11,857,653 B2
(45) Date of Patent: Jan. 2, 2024

(54) METHOD OF PROVIDING AN ORAL CARE BENEFIT USING A POORLY-SOLUBLE CALCIUM COMPOUND AND FLUORIDE

(71) Applicant: Johnson & Johnson Consumer Inc., Skillman, NJ (US)

(72) Inventors: Daniel Queiroz, Belle Mead, NJ (US); Chantel Tester, Belle Mead, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 769 days.

(21) Appl. No.: 16/222,339

(22) Filed: Dec. 17, 2018

(65) Prior Publication Data

US 2020/0188245 A1 Jun. 18, 2020

(51) Int. Cl.
| | |
|---|---|
| *A61K 8/21* | (2006.01) |
| *A61K 8/02* | (2006.01) |
| *A61K 8/19* | (2006.01) |
| *A61K 8/24* | (2006.01) |
| *A61K 8/44* | (2006.01) |
| *A61Q 11/00* | (2006.01) |

(52) U.S. Cl.
CPC .............. *A61K 8/21* (2013.01); *A61K 8/0204* (2013.01); *A61K 8/0216* (2013.01); *A61K 8/19* (2013.01); *A61K 8/24* (2013.01); *A61K 8/44* (2013.01); *A61Q 11/00* (2013.01)

(58) Field of Classification Search
CPC . A61Q 11/00; A61K 8/19; A61K 8/24; A61K 8/55; A61K 8/21; A61K 2800/92; A61K 9/006; A61K 9/0053; A61K 2800/88; A61K 2800/884; A61K 6/75; A61K 33/16; A61K 6/838; A61C 8/0006
See application file for complete search history.

(56) References Cited

U.S. PATENT DOCUMENTS

| | | | |
|---|---|---|---|
| 4,556,561 | A | 12/1985 | Brown et al. |
| 5,874,068 | A | 2/1999 | Engelman et al. |
| 2006/0171904 | A1 | 8/2006 | Vogel et al. |
| 2009/0202450 | A1 | 8/2009 | Prencipe |
| 2009/0202454 | A1* | 8/2009 | Prencipe ................. A61P 31/02 424/52 |
| 2010/0028273 | A1 | 2/2010 | Fischer et al. |
| 2011/0123462 | A1 | 5/2011 | Mordas et al. |
| 2011/0239736 | A1* | 10/2011 | Ramji .................... A61K 8/368 73/23.34 |
| 2016/0145203 | A1 | 5/2016 | Gambogi et al. |
| 2017/0319444 | A1 | 11/2017 | Dehghan et al. |
| 2018/0092817 | A1 | 4/2018 | Dehghan et al. |
| 2018/0140521 | A1 | 5/2018 | Geonnotti, III et al. |
| 2018/0140554 | A1 | 5/2018 | Wittorff et al. |

FOREIGN PATENT DOCUMENTS

| | | |
|---|---|---|
| JP | H08301742 A | 11/1996 |
| WO | WO 2014/124950 A1 | 8/2014 |

OTHER PUBLICATIONS

Bell, Janie, "Are Antacids Bad News for Your Mouth?", Patient Resources, pp. 1-2, Dec. 25, 2015. (Year: 2015).*
International Search Report; PCT/IB2019/060001; dated Feb. 14, 2020.

* cited by examiner

*Primary Examiner* — Lezah Roberts
(74) *Attorney, Agent, or Firm* — Darryl C. Little (57) ABSTRACT

Provided are methods of providing a benefit to the oral cavity by administering to the oral cavity a poorly-soluble calcium compound and subsequently introducing fluoride to the oral cavity.

9 Claims, 1 Drawing Sheet

METHOD OF PROVIDING AN ORAL CARE BENEFIT USING A POORLY-SOLUBLE CALCIUM COMPOUND AND FLUORIDE

FIELD OF THE INVENTION

The present invention relates to methods of providing a benefit to the oral cavity using a poorly-soluble calcium compound and fluoride. More specifically, the invention is related to methods of providing an oral care benefit, including for example enhancing remineralization and/or anti-caries benefits, by introducing to the oral cavity a poorly-soluble calcium compound prior to introducing fluoride into the oral cavity.

SUMMARY OF THE INVENTION

According to aspect, the present invention is directed to a method of providing a benefit to the oral cavity comprising administering to the oral cavity a poorly-soluble calcium compound and subsequently introducing fluoride to said oral cavity.

In one embodiment, the source of the poorly-soluble calcium compound is a tablet.

DETAILED DESCRIPTION OF THE INVENTION

Applicants have discovered significant advantages in providing benefits to the oral cavity using poorly-soluble calcium compounds and fluoride. In particular, the claimed methods tend to exhibit both significant remineralization and pH buffering, as compared to other methods including methods using highly-soluble calcium compounds.

As used herein, the term "poorly-soluble calcium compound" refers to any calcium-containing compound having a solubility in water at neutral pH of less than 0.5 g/L. In certain embodiments, the poorly-soluble calcium compound has a solubility of about 0.25 g/L or less, about 0.1 g/L or less, or about 0.05 g/L or less. Examples of suitable poorly-soluble calcium compounds include poorly-soluble calcium salts including, but not limited to, calcium phosphate, calcium carbonate, calcium oxalate, calcium silicate, combinations of two or more thereof, and the like. In certain preferred embodiments, the poorly-soluble calcium compound comprises calcium carbonate.

The poorly soluble calcium-containing compounds may be delivered to the oral cavity in any suitable form, including but not limited to a solid form, for example, in a powder, tablet, confection, chewing gum, and the like, or in liquid form, for example, in a mouthwash, mouth rinse, toothpaste, gel, and the like. In certain embodiments, the poorly soluble calcium compound is introduced to the oral cavity in the form of a tablet. In certain embodiments, the poorly soluble calcium compound is introduced to the oral cavity via mouthwash or mouthrinse.

The concentration of calcium in the delivery vehicle depends at least in part on the form of the selected delivery vehicle. Generally, it is desired to deliver a concentration of poorly soluble calcium in the oral tissue that is effective for reacting with the administered fluoride to form calcium-bound fluoride deposits in plaque, on teeth and in oral tissue. By way of example, to deliver these concentrations of poorly soluble calcium in the oral cavity, the calcium concentration in a pre-rinse that is used before a fluoride rinse or dentifrice preferably is between about 0.1 percent to about 20 percent, or from about 1 percent to about 15 percent, or from about 5 percent to about 10 percent by weight. When formulated as a tablet, the total calcium content is between about 0.1 percent to about 50 percent, or from about 1 percent to about 15 percent, or from about 1 percent to about 5 percent by weight. When formulated in a dentifrice, the calcium content is between about 0.2 percent to about 50 percent, or from about 1 percent to about 25 percent, or from about 5 percent to about 15 percent of poorly soluble calcium by weight.

In some embodiments, poorly soluble calcium-containing compounds may be delivered in the form of tablet, such as the tablets which generate a fluid that can be moved throughout the oral cavity as described in U.S. Patent Publication No. 20180140521 to Geonnotti III, et al., and U.S. Patent Publication No. 20180140554A1 to Wittorff, et al., herein incorporated by reference in their entirety.

In certain preferred embodiments, the tablets are chewable, dissolvable tablets, having a hardness that allows for biting and chewing the tablet by a user.

They may be of any suitable size/weight for use in generating a fluid for use in the methods. Weights such as greater than about 1 gram or greater, or about 1.2 grams or greater, or about 1.5 grams or greater. In certain preferred embodiments, the tablets are from about 1.0 grams to about 3 grams, or from about 1.1 grams to about 2.5 grams, or from about 1.5 grams to about 2 grams. The tablets may be of any appropriate thickness, including a thickness of from about 5 to about 15 millimeters (mm), or from about 6 to about 12 mm, from about 7 to about 8 mm. The tablets may also have a diameter, diagonal, or longest edge length of any suitable size including from about 5 to about 20 mm, or from about 10 to about 18 mm, or from about 12 to about 16 mm.

The tablets may be prepared via any of a variety of tableting methods known in the art. Conventional methods of tablet production include direct compression ("dry blending"), dry granulation followed by compression, wet granulation followed by drying and compression, application of energy to a blend of materials to be tableted, including applying heat, microwave, infrared, and other energies, combinations of two or more thereof, and the like.

The tablets may comprise any of a variety of materials suitable for use therein. In certain embodiments, the tablets comprise at least one carbohydrate. Examples of carbohydrates include but are not limited to sugars such as dextrose, dextrose monohydrate, lactose, glucose, fructose, maltodextrin, sucrose, corn syrup solids and mannose; carbohydrate alcohols, such as sugar alcohols including sorbitol, lactitol, xylitol, erythritol, mannitol, maltitol, isomalt, and polyols; and combinations of two or more thereof. In certain preferred embodiments, the tablets comprise one or more sugar alcohols selected from the group consisting of xylitol, erythritol, maltitol, and isomalt, including, for example, xylitol, maltitol and combinations thereof, or xylitol, erythritol, isomalt and combinations thereof including combinations of xylitol, erythritol, and isomalt. In certain preferred embodiments, the tablets comprise erythritol alone or in combination with one or more additional sugar alcohols. In certain preferred embodiments, the tablets comprise xylitol alone or in combination with one or more additional sugar alcohols. In other preferred embodiments, the tablets comprise one or more sugar alcohols selected from the group consisting of sorbitol, lactitol, xylitol, mannitol, maltitol, isomalt, and combinations two or more thereof.

In some embodiments, the carbohydrates in the tablet may be Zerose™ 16952F erythritol supplied by Cargill, or Zerose™ DC 16966 erythritol also supplied by Cargill. In certain embodiments, the tablets comprise both erythritols.

In certain embodiments, the tablets comprise a total amount of all carbohydrates in amount of at least 40% by weight of the tablet, including from about 40 to about 99%, or from about 75 to about 95%, or from about 80 to about 90% by weight of the tablets. In certain preferred embodiments, the carbohydrates comprise one or more sugar alcohols, and the tablet comprises a total amount of sugar alcohols of at least 40% by weight of the tablet, including from about 60 to 99%, or from about 80 to about 90% by weight of the tablets. In certain embodiments, the tablets comprise at least 20% of each of two or more carbohydrates, including at least 20% of xylitol and at least 20% of one or more other sugar alcohols. In certain embodiments, the tablet comprises from about 20-50% of xylitol, including mixtures comprising from about 20-50% xylitol and from about 20-50% of erythritol, and from about 20-40% of isomalt. In certain embodiments, the tablets comprise from about 20-50% xylitol and at least 20% of one other sugar alcohol selected from the group consisting of sorbitol, lactitol, mannitol, maltitol, isomalt, and combinations two or more thereof.

The tablets may be sugar-free. As will be readily understood by one of skill in the art, such tablets may contain sugar alcohols but are nevertheless substantially free of sugars such as glucose, dextrose, sucrose, or oligomers/polymers of sugar molecules.

In addition to poorly soluble calcium-containing compounds, the tablets may comprise one or more active ingredients for use in providing an oral care benefit. In certain embodiments, the active ingredients include, but are not limited to, any of a variety of actives for providing benefits such as mouth cleaning, including debris removal, antimicrobial, including anti-plaque, anti-gingivitis, and reduction in malodor, biofilm disruption, prevention of bacterial attachment, modification of oral microbial community structure, modification of the metabolic profile of oral microbes, antiviral activity, anti-inflammatory, pH balance, tooth whitening, stain prevention, anti-sensitivity, anti-caries, enamel strengthening, breath freshening, oral hydration/dry mouth relief, erosion repair and prevention, active delivery and retention, sensory enhancement, mouth feel alteration, pain relief, wound healing, and the like.

In addition, in certain embodiments, the tablets also comprise essential oils. Essential oils are volatile aromatic oils which may be synthetic or may be derived from plants by distillation, expression or extraction, and which usually carry the odor or flavor of the plant from which they are obtained. Useful essential oils may provide antiseptic activity. Some of these essential oils also act as flavoring agents. Useful essential oils include but are not limited to citra, thymol, menthol, methyl salicylate (wintergreen oil), eucalyptol, carvacrol, camphor, anethole, carvone, eugenol, isoeugenol, limonene, osimen, n-decyl alcohol, citronel, a-salpineol, methyl acetate, citronellyl acetate, methyl eugenol, cineol, linalool, ethyl linalaol, safrola vanillin, spearmint oil, peppermint oil, lemon oil, orange oil, sage oil, rosemary oil, cinnamon oil, pimento oil, laurel oil, cedar leaf oil, gerianol, verbenone, anise oil, bay oil, benzaldehyde, bergamot oil, bitter almond, chlorothymol, cinnamic aldehyde, citronella oil, clove oil, coal tar, eucalyptus oil, guaiacol, tropolone derivatives such as hinokitiol, avender oil, mustard oil, phenol, phenyl salicylate, pine oil, pine needle oil, sassafras oil, spike lavender oil, storax, thyme oil, tolu balsam, terpentine oil, clove oil, and combinations thereof.

In certain preferred embodiments, the tablet comprises one or more bioactive essential oils selected from the group consisting of menthol, thymol, eucalyptol, and methyl salicylate. In certain preferred embodiments, the tablet comprises menthol and at least one other essential oil selected from thymol, eucalyptol, and methyl salicylate. In certain preferred embodiments, the tablet comprises menthol and eucalyptol, menthol, eucalyptol and thymol, or menthol, eucalyptol, thymol, and methyl salicylate. Thymol, [$(CH_3)_2CHC_6H_3(CH_3)OH$, also known as isopropyl-m-cresol], is only slightly soluble in water but is soluble in alcohol, and its presence is one of the reasons alcohol was necessary in the well-established, high alcohol commercial mouth rinses. Methyl salicylate, [$C_6H_4OHCOOCH_3$, also known as wintergreen oil], additionally provides flavoring to the together with its antimicrobial function. Eucalyptol ($C_{10}H_{18}O$, also known as cineol) is a terpene ether and provides a cooling, spicy taste. Eucalyptol may be used in place of thymol in certain formulations in the same amount if desired. Menthol ($CH_3C_6H_9(C_3H_7)OH$), also known as hexahydrothymol) is also only slightly soluble in alcohol, and is fairly volatile. Menthol, in addition to any antiseptic properties, provides a cooling, tingling sensation.

Other suitable antimicrobial agents include Halogenated Diphenyl Ethers, 2',4,4'-trichloro-2-hydroxy-diphenyl ether (Triclosan), 2,2'-dihydroxy-5,5'-dibromo-diphenyl ether, Halogenated Salicylanilides, 4'5-dibromosalicylanilide, 3,4', 5-trichlorosalcylanilide, 3,4',5-tribromosalicylanilide, 2,3,3', 5-tetrachlorosalicylanilide, 3,3',5-tetrachlorosalicylanilide, 3,5, dibromo-3'-trifluoromethyl salicylanilide, 5-n-octanoyl-3'-trifluoromethyl salicylanilide, 3,5-dibromo-4'-trifluoromethyl salicylanilide, 3,5-dibromo-3'-trifluoro methyl salicylanilide (Flurophene), Benzoic Esters, Methyl-p-Hydroxybenzoic Ester, Ethyl-p-Hydroxybenzoic Ester, Propyl-p-Hydroxybenzoic Ester, Butyl-p-Hydroxybenzoic Ester, Halogenated Carbanilides, 3,4,4'-trichlorocarbanilide, 3-trifluoromethyl-4,4'-dichlorocarbanilide 3,3',4-trichlorocarbanilide, Phenolic Compounds (including phenol and its homologs, mono- and poly-alkyl and aromatic halo (e.g. F, Cl, Br, I)-phenols, resorcinol and catechol and their derivatives and bisphenolic compounds), 2 Methyl-Phenol, 3 Methyl-Phenol, 4 Methyl-Phenol, 4 Ethyl-Phenol, 2,4-Dimethyl-Phenol, 2,5-Dimethyl-Phenol, 3,4-Dimethyl-Phenol, 2,6-Dimethyl-Phenol, 4-n-Propyl-Phenol, 4-n-Butyl-Phenol, 4-n-Amyl-Phenol, 4-tert-Amyl-Phenol, 4-n-Hexyl-Phenol, 4-n-Heptyl-Phenol, 2-Methoxy-4-(2-Propenyl)-Phenol (Eugenol), Mono- And Poly-Alkyl And Aralkyl Halophenols, Methyl-p-Chlorophenol, Ethyl-p-Chlorophenol, n-Propyl-p-Chlorophenol, n-Butyl-p-Chlorophenol, n-Amyl-p-Chlorophenol, sec-Amyl-p-Chlorophenol, n-Hexyl-p-Chlorophenol, Cyclohexyl-p-Chlorophenol, n-Heptyl-p-Chlorophenol, n-Octyl-p-Chlorophenol, O-Chlorophenol, Methyl-o-Chlorophenol, Ethyl-o-Chlorophenol, n-Propyl-o-Chlorophenol, n-Butyl-o-Chlorophenol, n-Amyl-o-Chlorophenol tert-Amyl-o-Chlorophenol, n-Hexyl-o-Chlorophenol, n-Heptyl-o-Chlorophenol, p-Chlorophenol, o-Benzyl-p-Chlorophenol, o-Benzyl-m-methyl-p-Chlorophenol o-Benzyl-m,m-dimethyl-p-Chlorophenol, o-Phenylethyl-p-Chlorophenol, o-Phenylethyl-m-methyl-p-Chlorophenol, 3-Methyl-p-Chlorophenol, 3,5-Dimethyl-p-Chlorophenol, 6-Ethyl-3-methyl-p-Chlorophenol, 6-n-Propyl-3-methyl-p-Chlorophenol, 6-iso-Propyl-3-methyl-p-Chlorophenol, 2-Ethyl-3,5-dimethyl-p-Chlorophenol, 6-sec Butyl-3-methyl-p-Chlorophenol, 2-iso-Propyl-3,5-dimethyl-p-Chlorophenol, 6-Diethylmethyl-3-methyl-p-Chlorophenol, 6-iso-Propyl-2-ethyl-3-methyl-p-Chlorophenol, 2-sec Amyl-3,5-dimethyl-p-Chlorophenol, 2-Diethylmethyl-3,5-dimethyl-p-Chlorophenol, 6-sec Octyl-3-methyl-p-Chlorophenol, p-Bromophenol, Methyl-p-Bromophenol, Ethyl-p-Bromophenol, n-Propyl-p-Bromophenol, n-Butyl-p-Bromophenol, n-Amyl-p-Bromophenol, sec-Amyl-p-Bromophenol, n-Hexyl-p-Bromophenol, cyclohexyl-p-Bromophenol, o-Bromophenol, tert-Amyl-o-Bromophenol, n-Hexyl-o-Bromophenol, n-Propyl-m,m-Dimethyl-o-Bromophenol, 2-Phenyl Phenol, 4-chloro, 2-methyl phenol, 4-chloro-3-methyl phenol, 4-chloro-3,5-dimethyl phenol, 2,4-dichloro-3,5-dimethylphenol, 3,4,5,6-terabromo-2-methylphenol, 5-methyl-2-pentylphenol, 4-isopropyl-3-methylphenol, 5-chloro-2-hydroxydiphenylemthane, Resorcinol And Its Derivatives, Resorcinol, Methyl-Resorcinol, Ethyl-Resorcinol, n-Propyl-Resorcinol, n-Butyl-Resorcinol, n-Amyl-Resorcinol, n-Hexyl-Resorcinol, n-Heptyl-Resorcinol, n-Octyl-Resorcinol, n-Nonyl-Resorcinol, Phenyl-Resorcinol, Benzyl-Resorcinol, Phenylethyl-Resorcinol, Phenylpropyl-Resorcinol, p-Chlorobenzyl-Resorcinol, 5-Chloro-2,4-Dihydroxydiphenyl Methane, 4'-Chloro-2,4-Dihydroxydiphenyl Methane, 5-Bromo-2,4-Dihydroxydiphenyl Methane, 4'-Bromo-2,4-Dihydroxydiphenyl Methane, Bisphenolic Compounds, Bisphenol A, 2,2'-methylene bis(4-chlorophenol), 2,2'-methylene bis(3,4,6-trichlorophenol) (hexachlorophene), 2,2'-methylene bis(4-chloro-6-bromophenol), bis(2-hydroxy-3,5-dichlorophenyl) sulfide, bis (2-hydroxy-5-chlorobenzyl) sulfide, menthoxy-1,2-propanediol, ortho-methoxy cinnamic aldehyde, menthyl-3-hydroxybutanoate, combinations of two or more thereof, and the like.

Other antimicrobial agents include, but are not limited to: hexetidine; fatty acid compounds such as caproic acid, caprilic acid, capric acid, lauric acid, myristic acid, myristoleic acid, palmitic acid, palmitoleic acid, stearic acid, oleic acid, elaidic acid, linoleic acid, linolenic acid, linolelaidic acid, arachidonic acid vitamin E, vitamin E acetate, apigenin and mixtures thereof; long chain fatty alcohols such as described in US Patent publication US 20110123462 to Mordas et al., herein incorporated by reference in its entirety, (examples of which include, but are not limited to 1-decen-3-ol; cis-4-decen-1-ol, trans-2-decen-1-ol, cis-2-nonen-1-ol, cis-4-decenal, trans-2-decenal, cis-7-decenal, cis-5-octen-1-ol, trans-2-octen-1-ol, 1-octen-3-ol, cis-3-nonen-1-ol, trans-2-nonen-1-ol, cis-6-nonen-1-ol, 9-decen-1-ol, trans-2-undecen-1-ol, trans-2-dodecen-1-ol, trans-2-octenal, trans-2-nonenal, 6-nonenal, cis-2-decenal, trans-2-undecenal, trans-2-dodecenal, cis-3-octen-1-ol, 3-octen-2-ol, 10-undecen-1-ol, trans-2-tridecen-1-ol, stereoisomers thereof and mixtures thereof); cyclic sesquiterpene alcohols, such as farnesol; N'-alkyl-L-arginine alkyl ester (e.g., Lauroyl Arginine Ethyl Ester) and salts such as described in U.S. Pat. No. 5,874,068 to Engelman et al., herein incorporated by reference in its entirety; Amino acid derivative compounds as described in U.S. Patent Publication No. 20160145203 to Gambogi, et al., herein incorporated by reference in its entirety; antimicrobial peptides, such as retrocyclin (RC101), protegrin-1 (PG1) or KSL-W; and surfactants, including cationic surfactants such as cetylpyridinium chloride, chlorhexedine and mixtures thereof. Additionally, antimicrobial extracts of certain botanical or fruits may be included, including proanthocyanidins (PACs) found in cranberry such as, flavan-3-ols (and polymers of), procyanidins (and polymers of), terpenes (and polymers of), hydroxybenzole acids, hydroxycinnamic acids, anthocyanidins (and polymers of), flavonols (and polymers of), and other cyanidins and peonidins. Oils such as peppermint oil and sage oil are also useful herein.

Other suitable actives include fluoride ion sources such as sodium fluoride, sodium monofluorophosphate, stannous fluoride, and amine fluorides (providing, for example, about 1-5000 ppm of fluoride ion, optionally about 200-1150 ppm of fluoride ion); anti-calculus agents, such as water-soluble pyrophosphate salts such as alkali metal pyrophosphates, polyacrylates and copolymers of maleic anhydride or acid and methyl vinyl ether, polyamino propane sulfonic acid (AMPS), zinc citrate trihydrate, polypeptides (such as polyaspartic and polyglutamic acids), and mixtures of two or more thereof, water-soluble pyrophosphate salts such as alkali metal pyrophosphates; chelating agents such as tartaric acid and pharmaceutically-acceptable salts thereof, citric acid and alkali metal citrates and mixtures thereof tooth desensitization agents which reduce tooth sensitivity including potassium salts such as potassium nitrate and potassium chloride and strontium salts such as strontium chloride and strontium acetate; tooth whitening agents and vitamins such as vitamin A; as well as pigments and colorants such as inorganic white pigments, inorganic colored pigments, pearling agents, filler powders and the like, as well as talc, mica, magnesium carbonate, magnesium silicate, aluminum magnesium silicate, silica, titanium dioxide, zinc oxide, red iron oxide, brown iron oxide, yellow iron oxide, black iron oxide, ferric ammonium ferrocyanide, manganese violet, ultramarine, nylon powder, polyethylene powder, methacrylate powder, polystyrene powder, silk powder, crystalline cellulose, starch, titanated mica, iron oxide titanated mica, bismuth oxychloride, and mixtures of two or more thereof.

Enzymes are another type of active that may be used in the tables. Useful enzymes include those that belong to the category of proteases, lytic enzymes, plaque matrix inhibitors and oxidases: Proteases include papain, pepsin, trypsin, ficin, bromelin; cell wall lytic enzymes include lysozyme; plaque matrix inhibitors include dextranases, mutanases; and oxidases include glucose oxidase, lactate oxidase, galactose oxidase, uric acid oxidase, laccase, peroxidases including horse radish peroxidase, myeloperoxidase, lactoperoxidase, chloroperoxidase. The oxidases also have whitening/cleaning activity, in addition to antimicrobial properties.

Ingredients which are metabolized by oral bacteria to cause a benefit effect in the oral cavity may also be included in these tablets, including arginine, arginine monohydrochloride, and inulin-type fructans, maltodextrin, fructooligosaccharides and galactooligosaccharides. Additionally, these tablets may be used to deliver probiotic strains of bacteria, including certain species of lactobacilli and bifidobacteria, *Saccharomyces* spp, streptococci, enterococci and commensal *Escherichia coli*.

The tablet may also be used to deliver pharmaceutical actives to treat oral diseases or disease symptoms which occur in the oral cavity or the oropharynx, such as anesthetics, antibiotics, antifungals, antiviral, and anti-inflammatory compounds.

In certain embodiments, the tablets for use in the present invention may comprise any of a variety of salivation agents (also known as salivary stimulants or salivary agents). Suitable salivation agents include food organic acids such as citric, lactic, malic, succinic, ascorbic, adipic, fumaric, tartaric acids, parasympathomimetic drugs, such as choline esters like pilocarpine hydrochloride, or cholinesterase inhibitors, and combinations of two or more thereof. In certain preferred embodiments, the salivation agents comprise citric acid, succinic acid, or a combination thereof alone or in combination with other salivation agents. In certain preferred embodiments, the salivation agent comprises jambu oleoresin extract. The salivation agent may be present in any suitable amount for use in the present invention including, from about 0.001 to about 5% by weight of the tablet, including from about 0.01 to about 3%, from about 0.01 to about 1% from about 0.01 to about 0.5%, from about 0.01 to about 0.25%, and from about 0.01 to about 0.1% by weight of the tablet.

The tablets for use in the present invention may comprise any of a variety of additional ingredients suitable for use in the tablets including, for example, sweeteners, lubricants, fillers, adsorbents, disintegrants, glidants, superdisintegrants, flavor and aroma agents, antioxidants, preservatives, texture enhancers, coloring agents, and the like, and mixtures of two or more thereof.

In certain embodiments, the tablets may comprise additional sweeteners including, but not limited to, synthetic or natural sugars; artificial sweeteners such as saccharin and its salts including sodium saccharin, aspartame, acesulfame and its salts including potassium acesulfame, thaumatin, glycyrrhizin, sucralose, dihydrochalcones, alitame, miraculin, monellin, stevioside, and combinations of two or more thereof. In certain preferred embodiments, the tablets comprise sucralose, potassium acesulfame, or a combination thereof. The tablets may comprise any suitable total amounts of additional sweeteners including from 0.001 to about 8% by weight, including from about 0.02 to about 8%, from about 0.1 to about 3%, from about 0.1 to about 1%, and from about 0.1 to about 0.5% by weight of the tablet.

The tablets may also include lubricant materials in certain embodiments. Suitable lubricants include, but are not limited to, long chain fatty acids and their salts, such as magnesium stearate and stearic acid, talc, glycerides waxes, and mixtures thereof. Such materials may be present in any suitable amount including from about 0.01 to about 5%, including from about 0.1 to about 5%, from about 0.5 to about 3%, including from about 0.5 to about 2% by weight of the tablet.

Suitable fillers include, but are not limited to, water insoluble plastically deforming materials (e.g., microcrystalline cellulose or other cellulosic derivatives), and mixtures thereof. Suitable adsorbents include, but are not limited to, water-insoluble adsorbents such as dicalcium phosphate, tricalcium phosphate, silicified microcrystalline cellulose (e.g., such as distributed under the PROSOLV brand (PenWest Pharmaceuticals, Patterson, N.Y.)), magnesium aluminometasilicate (e.g., such as distributed under the NEUSILIN brand (Fuji Chemical Industries (USA) Inc., Robbinsville, N.J.)), clays, silicas, bentonite, zeolites, magnesium silicates, hydrotalcite, veegum, and mixtures thereof. Suitable disintegrants include, but are not limited to, sodium starch glycolate, cross-linked polyvinylpyrrolidone, cross-linked carboxymethylcellulose, starches, microcrystalline cellulose, and mixtures thereof.

Examples of superdisintegrants include, but are not limited to, croscarmellose sodium, sodium starch glycolate and cross-linked povidone (crospovidone). In one embodiment, the tablet contains up to about 5% by weight of such superdisintegrant.

Examples of flavors and aromatics include, but are not limited to, essential oils including distillations, solvent extractions, or cold expressions of chopped flowers, leaves, peel or pulped whole fruit containing mixtures of alcohols, esters, aldehydes and lactones; essences including either diluted solutions of essential oils, or mixtures of synthetic chemicals blended to match the natural flavor of the fruit (e.g., strawberry, raspberry and black currant); artificial and natural flavors of brews and liquors, e.g., cognac, whisky, rum, gin, sherry, port, and wine; tobacco, coffee, tea, cocoa, and mint; fruit juices including expelled juice from washed, scrubbed fruits such as lemon, orange, and lime; spear mint, pepper mint, wintergreen, cinnamon, cacoe/cocoa, vanilla, liquorice, menthol, eucalyptus, aniseeds nuts (e.g., peanuts, coconuts, hazelnuts, chestnuts, walnuts, colanuts), almonds, raisins; and powder, flour, or vegetable material parts including ginger.

Examples of antioxidants include, but are not limited to, tocopherols, ascorbic acid, sodium pyrosulfite, butylhydroxytoluene, butylated hydroxyanisole, edetic acid, and edetate salts, and mixtures thereof.

Examples of preservatives include, but are not limited to, citric acid, tartaric acid, lactic acid, malic acid, acetic acid, benzoic acid, and sorbic acid, and mixtures thereof. Examples of texture enhancers include, but are not limited to, pectin, polyethylene oxide, and carrageenan, and mixtures thereof. In one embodiment, texture enhancers are used at levels of from about 0.1% to about 10% percent by weight.

In one embodiment, the tablets further contain one or more effervescent couples. In one embodiment, effervescent couple contains one member from the group consisting of sodium bicarbonate, potassium bicarbonate, calcium carbonate, magnesium carbonate, and sodium carbonate, and one member selected from the group consisting of citric acid, malic acid, fumaric acid, tartaric acid, phosphoric acid, and alginic acid. In one embodiment, the combined amount of the effervescent couple(s) in the powder blend/tablet is from about 2 to about 20 percent by weight, such as from about 2 to about 10 percent by weight of the total weight of the powder blend/tablet.

In some embodiments, the tablets may be made by mixing its ingredients and heating them until they melt into a syrup, then exposing the mixture to pressurized carbon dioxide gas (about 600 pounds per square inch, or psi) and allowing it to cool. The process causes tiny high-pressure bubbles to be trapped inside the candy. When the tablet is placed in the mouth and comes into contact with saliva, the tablet breaks and dissolves, releasing the carbon dioxide from the bubbles, resulting in a popping and sizzling sound and leaving a slight tingling sensation.

The tablets are substantially free of gum bases as used conventionally to manufacture gums, as opposed to chewable, dissolvable tablets. In preferred embodiments, the tablets of the present invention are not sufficiently heated to form hard candies nor lozenges as such terms and their manufacture is understood in the art and which product forms are intended to dissolve more slowly than chewable, dissolvable tablets.

Any suitable fluoride-containing compounds/sources of fluoride or may be used in the methods of the present invention. Examples of suitable compounds used as fluoride sources include sodium fluoride, sodium monofluorophosphate, stannous fluoride, amine fluorides, titanium tetrafluoride, combinations of two or more thereof, and the like.

The fluoride-containing compounds may be delivered to the oral cavity in any suitable form, including but not limited to a solid form, for example, in a powder, tablet, confection, chewing gum, and the like, or in liquid form, for example, in a mouthwash, mouth rinse, toothpaste, gel, and the like. In certain embodiments, the fluoride-containing compound is introduced to the oral cavity via a tablet. In certain embodiments, the fluoride-containing compound is introduced to the oral cavity via mouthwash. Any of a variety of commercially available fluoride containing products, e.g. rinses, toothpastes, and the like, may be used herein.

The concentration of fluoride in the delivery vehicle/product depends at least in part on the form of the selected delivery vehicle. Generally, it is desired to deliver a concentration of fluoride in the oral tissue that is effective for reacting with the administered calcium to form calcium-bound fluoride deposits in plaque, on teeth and in oral tissue. The delivery vehicle should provide, for example, about 0.01-5000 ppm of fluoride ion, or about 100-1500 ppm of fluoride ion, or about 100-500 ppm of fluoride ion. By way of example, to deliver these concentrations of fluoride in the oral cavity, the fluoride concentration in a fluoride rinse is between about 50 ppm to about 1000 ppm. When formulated as a tablet, the total fluoride content preferably is between about 0.01 ppm to about 10 ppm fluoride. When formulated in a dentifrice, the fluoride content preferably is between about 500 ppm to about 5000 ppm, or about 500 to about 1500 ppm of fluoride.

The embodiments of the present invention can be used with any commercial fluoride product (e.g., mouthwash, mouth rinse, dentifrice, gels/foams, varnishes, lozenges, tablets, chewing gum, medical supplements) specifically formulated to take advantage of the chemistry described herein, or in regions which have water fluoridation.

In some embodiments, fluoride compounds may be delivered in the form of a mouthwash or dentifrice. Mouthwashes and rinses are usually antiseptic solutions intended to reduce the microbial load in the oral cavity, although other mouthwashes might be given for other reasons such as for their analgesic, anti-inflammatory or anti-fungal action. Additionally, some rinses act as saliva substitutes to neutralize acid and keep the mouth moist in xerostomia (dry mouth). Cosmetic mouth rinses temporarily control or reduce bad breath and leave the mouth with a pleasant taste.

Fluoride mouthwashes and rinses typically use the sodium fluoride form, though stannous fluoride may also be used. They can be professionally-applied by a dental professional or used at home. The most common fluoride compound used in mouth rinse is sodium fluoride. Fluoride mouth rinses range from about 0.02% to about 0.2% (about 100 to about 1,000 ppm) in concentration, or about 0.02% to about 0.1% In some embodiments, daily fluoride rinses use a fluoride content of about 0.02%. After a fluoride mouth rinse treatment, the fluoride in the mouth rinse is retained in the saliva.

Toothpaste is a paste or gel dentifrice used with a toothbrush to clean and maintain the aesthetics and health of teeth. Toothpaste is used to promote oral hygiene: it is an abrasive that aids in removing dental plaque and food from the teeth, assists in suppressing halitosis, and delivers active ingredients.

Fluoride toothpastes may contain up to about 1.1% (5,000 ppm) fluoride in the form of sodium fluoride, or about 0.454% stannous fluoride. Typically, toothpaste has between about 0.22% (1,000 ppm) and about 0.312% (1,450 ppm) fluoride in the form of sodium fluoride or sodium monofluorophosphate. Most toothpastes with fluoride contain mild abrasives to remove heavier debris and light surface staining. These abrasives include calcium carbonate, silica gels, magnesium carbonates and phosphate salts.

Fluoride is available in several forms during toothbrushing. It is available as a free ionic fluoride which can react with the tooth structure, interfere with the metabolism of bacteria in plaque, or absorb to the oral mucosa. It is also available as profluoride compounds which can precipitate in the mouth during toothbrushing and release ionic fluoride.

Anti-sensitivity toothpastes with fluoride are also available for those who have sensitive teeth. Some anti-sensitivity toothpastes with fluoride on the market contain ingredients called strontium chloride or potassium nitrate which help to alleviate tooth sensitivity.

In some embodiments, fluoride containing foams/gels, varnishes, lozenges, of supplements may be used. Professionally-applied, or home-applied fluoride containing gels and foams may also be used. Typically, these fluoride gels include 2.0% neutral sodium fluoride and 1.23% acidulated phosphate fluoride. They are usually applied using a foam mouth tray which is held in the mouth by gently biting down. The application usually lasts for approximately four minutes. Some gels are made for home application with the use of a custom tray. The user holds a fluoride treatment against their teeth overnight or several minutes during the day. The concentration of fluoride in these gels is much lower than in professional products, typically containing between about 0.15% and 0.5% about fluoride.

Fluoride varnish has practical advantages over gels in ease of application and use of smaller volume of fluoride than required for gel applications. The principle of fluoride varnish is to apply fluoride salt in a very high concentration (approximately 50,000 ppm) directly onto the surface of the teeth. Fluoride varnish is a resin-based application that is designed to stay on the surface of the teeth for several hours. As this varnish rests on the tooth's surface, saliva dissolves the fluoride salt, which in turn allows fluoride ions to be released. Later, the fluoride is re-released into the oral cavity from these reservoirs which acts as protection for the teeth against cavities.

Fluoridated lozenges and medical fluoride supplements may also be used as the fluoride source in the present invention. Fluoridated lozenges contain about 1 mg fluoride each and are meant to be held in the mouth and sucked. The dissolved lozenge is swallowed slowly, so the use of lozenges is both a topical and a systemic therapy. Medical fluoride supplements are typically in the form of tablets, lozenges, or liquids (including fluoride-vitamin preparations).

In some embodiments, the fluoride source in the present invention could be fluoridated water. Water fluoridation is the controlled addition of fluoride to a public water supply reduce tooth decay. Its use in the U.S. began in the 1940s and is now used for about two-thirds of the U.S. population on public water systems and for about six percent of people worldwide. It is the most cost-effective way to induce fluoride into the oral cavity.

In use, the poorly soluble calcium compounds are orally administered in a delivery vehicle prior to the administration of the fluoride. In some embodiments, the poorly soluble calcium delivery vehicle is used just prior to the use of a fluoride-containing product. In these cases, the fluoride-containing compound is used as soon as practicable after use of the poorly soluble calcium compound delivery vehicle. In other embodiments, the administration of the fluoride-containing product is significantly after administration of the poorly soluble calcium compound. The administration of the fluoride-containing product may be one minute, or five minutes, or ten minutes, or thirty minutes, or one hour, or two hours, or four hours, or eight hours, or twelve hours or more after administration of the poorly soluble calcium compound or other times sufficient to allow most or all of the calcium to migrate from the oral cavity into the oral tissue.

In one embodiment, the fluoride-containing compound is administered about one minute, or ten minutes, or twenty minutes, or one hour or more after the administration of the poorly soluble calcium-containing compound.

In some embodiments, the vehicle with the poorly soluble calcium-containing compound is administered at numerous points in the day, with the fluoride-containing compound being administered at numerous points in the day, or only once a day. Healthy human saliva has a pH of 7.4. When acidic foods and drinks are consumed, the pH within the mouth decreases and can cause the pH in the dental plaque to fall rapidly below 5.0. This happens through the production of acids as the bacteria metabolize the ingested nutrients. Tooth decay can occur when the pH level in the mouth is 5.5 or below. When the mouth undergoes dramatic or long-lasting periods of low pH, it can cause cavity-causing bacteria to grow. Dental plaque that is kept at 7.0 or greater does not experience a shift to cavity-causing bacteria even when exposed to sugar.

Calcium containing compounds, as they dissolve, may raise the pH in the oral cavity. The slow dissolution of poorly soluble calcium sources as discussed herein in the oral cavity can act as a buffer to prevent the rapid fall of pH to 5.5 or below. In some embodiments, a user can administer the poorly soluble calcium compound delivery vehicle immediately, or soon after ingesting food, such as a meal or snack. For example, within one minute, or two minutes, or five minutes, or ten minutes, or fifteen minutes, or thirty minutes after ingesting food.

So, in some embodiments, the poorly soluble calcium compound delivery vehicle is administered two, or three, or four, or six, or eight or more times over the course of a day such as after meals or snacks, to help maintain poorly soluble calcium compound in plaque, on teeth, and in oral tissue. Fluoride compound may also be administered one, two, or three, or four or more times in conjunction with the administration poorly soluble calcium compound.

For example, a user may administer the poorly soluble calcium compound delivery vehicle after each meal or snack and administer the fluoride compound after one or more of the meals/snacks, or just at the end of the day.

In other embodiments, the order of administration may be reversed (i.e. fluoride is administered prior to administration of calcium). Such a reverse system also is expected provide an increase in oral deposition of Ca—F. As with the administration of calcium followed by fluoride, it may be desirable to delay the administration of calcium subsequent to the administration of fluoride.

In some embodiments, methods of the present invention comprise introducing into the oral cavity a tablet of the present invention. Any of a variety of know means may be used in the introducing step. For example, a tablet may be placed by hand into a user's mouth, the tablet may be introduced via an applicator, packaging, container, dosing apparatus, or other article or machine suitable for such purpose.

In certain embodiments, chewing the tablet generates a fluid in the oral cavity while the tablet dissolves, generating a fluid comprising ingredients from the tablet. The tablet may be chewed for any time sufficient to generate fluid in accord with embodiments comprising a chewing step, including, for example, chewing for at least five seconds, including at least ten seconds, at least fifteen seconds, at least twenty seconds, or at least thirty seconds. In certain preferred embodiments, the tablet is chewed for about ten seconds or for at least ten seconds.

The fluid generated may be forced around the oral cavity. The forcing step comprises applying any suitable amount of force within the oral cavity to move fluid in any one or more directions, e.g., from side to side, up, down, back, forth, forward, back, around, onto and/or through teeth, gums, cheek, and/or another surface in the oral cavity. In certain embodiments, the fluid is forced (a) from a lingual surface of the oral cavity toward or onto a buccal and/or labial surface of the oral cavity, (b) from a buccal and/or labial surface of the oral cavity toward or onto a lingual surface of the oral cavity, or both (a) and (b). In certain embodiments, the fluid is forced around the oral cavity using muscular movements of the cheeks and/or tongue. In certain embodiments, the fluid is forced around the oral cavity with the lips closed. In certain preferred embodiments, the forcing step comprises forcing at least a portion of the fluid generated around the mouth, with lips closed, using muscular movements of the cheeks and tongue. The fluid may be forced in any suitable manner in accord with the present invention, including, for example, by swishing, rinsing, washing, swirling, gargling, agitating, threshing, sloshing, irrigating, actuating, gushing, douching, swooshing, splooshing, squooshing, pushing, maneuvering, mixing, twisting, flowing, bathing, circulating, distributing, dispersing, wetting, moving, and the like, the fluid in any one or more directions, or otherwise using the fluid as a mouthwash, mouth rinse, or other liquid oral care product. The fluid may be forced/moved within the oral cavity for any suitable period of time including at for at least five seconds, including at least ten seconds, at least fifteen seconds, at least twenty seconds, or at least thirty seconds. In certain preferred embodiments, the fluid is agitated for about thirty seconds or for at least thirty seconds.

In certain embodiments, the fluid generated in the present methods may be swallowed/ingested by a user or may be expelled/spit out after the moving step. In certain preferred embodiments, the methods comprise swallowing at least a portion of the fluid. However, upon swallowing/ingesting the fluid, some of the poorly soluble calcium-containing compound remains in the oral cavity, such as in or in the plaque, teeth or oral tissue.

EXAMPLES

The present invention will be further understood by reference to the following specific examples that are illustrative of the methods of the present invention. It is to be understood that many variations of the methods would be apparent to those skilled in the art. The following examples are only illustrative.

Example 1: pH Cycling Study

A pH cycling study was performed. The study was developed to simulate the spike in acid production after three meals during the course of a day.

Bovine enamel specimens were polished and artificial lesions formed by immersion of the specimens in a lesion forming solution consisting of 0.1 M lactic acid and 0.2% Carbopol C907 which was 50% saturated with hydroxyapatite and adjusted to pH 5.0. The average specimen surface microhardness (SMH) was determined from four indentations on the surface of each specimen, using a Vickers hardness indenter at a load of 200 g for 15 seconds. The lesion surface hardness range was 25-45 VEIN and average lesion depth was approximately 70 microns. Specimens were divided into subgroups of 18 specimens balanced by post-demineralization surface microhardness (SMH) values.

Remineralization efficacy was evaluated under two different cyclic treatment regimens. Both regimens consisted of three one-minute fluoride treatment periods (100 ppm, pH=6.5), and three one-hour acid challenges in the lesion forming solution, with calcium introduced during the acid challenges. For the remaining time (approximately 21 hours), the specimens were in artificial saliva consisting of 0.213 g/L calcium chloride dihydrate, 0.738 g/L potassium phosphate monobasic, 0.738 g/L potassium chloride, 0.381 g/L sodium chloride, and 2.2 g/L of porcine mucin.

The difference between the two treatment regimens was the relative order of the fluoride treatments and the acid challenges. In Regimen I, shown in Table 1, the demineralization event (Demin: Lactic Acid Challenge) occurred first, followed by the remineralization event (Remin: Artificial Saliva Soak). In Regimen II, shown in Table 2, the order of events was reversed, and the remineralization event occurred first, followed by the demineralization event.

TABLE 1 pH cycling Regimen I

| Time | Event |
|---|---|
| 9:00-9:20 a.m. | Demin: Lactic Acid Challenge (15 mL) |
| 9:20-9:30 a.m. | +Calcium Treatment |
| 9:30-9:40 a.m. | +5 mL Lactic Acid |
| 9:40-9:50 a.m. | +5 mL Lactic Acid |
| 9:50-10:00 a.m. | +5 mL Lactic Acid |
| 10:00-10:30 a.m. | Remin: Artificial Saliva Soak |
| 10:30-10:32 a.m. | Fluoride Treatment |
| 10:32 a.m.-12:00 p.m. | Remin: Artificial Saliva Soak |
| 12:00-12:20 p.m. | Demin: Lactic Acid Challenge (15 mL) |
| 12:20-12:30 p.m. | +Calcium Treatment |
| 12:30-12:40 p.m. | +5 mL Lactic Acid |
| 14:40-12:50 p.m. | +5 mL Lactic Acid |
| 12:50-1:00 p.m. | +5 mL Lactic Acid |
| 1:00-1:30 p.m. | Remin: Artificial Saliva |
| 1:30-1:32 p.m. | Fluoride Treatment |
| 1:32-3:00 p.m. | Remin: Artificial Saliva Soak |
| 3:00-3:20 p.m. | Demin: Lactic Acid Challenge (15 mL) |
| 3:20-3:30 p.m. | +Calcium Treatment |
| 3:30-3:40 p.m. | +5 mL Lactic Acid |
| 3:40-3:50 p.m. | +5 mL Lactic Acid |
| 3:50-4:00 p.m. | +5 mL Lactic Acid |
| 4:00-4:30 p.m. | Remin: Artificial Saliva Soak |
| 4:30-4:32 p.m. | Fluoride Treatment |
| 4:32 p.m.-9:00 a.m. | Remin: Overnight Artificial Saliva Soak |

TABLE 2 pH cycling Regimen II

| Time | Event |
|---|---|
| 9:00-9:02 a.m. | Fluoride Treatment |
| 9:02-9:30 a.m. | Remin: Artificial Saliva Soak |
| 9:30-9:50 a.m. | Demin: Lactic Acid Challenge (15 mL) |
| 9:50-10:0 a.m. | +Calcium Treatment |
| 10:00-10:10 a.m. | +5 mL Lactic Acid |
| 10:10-10:20 a.m. | +5 mL Lactic Acid |
| 10:20-10:30 a.m. | +5 mL Lactic Acid |
| 10:30 a.m.-12:00 p.m. | Remin: Artificial Saliva Soak |
| 12:00-12:02 p.m. | Fluoride Treatment |
| 12:02-12:30 | Remin: Artificial Saliva Soak |
| 12:30-12:50 p.m. | Demin: Lactic Acid Challenge (15 mL) |
| 12:50-1:00 p.m. | +Calcium Treatment |
| 1:00-1:10 p.m. | +5 mL Lactic Acid |
| 1:10-1:20 p.m. | +5 mL Lactic Acid |
| 1:20-1:30 p.m. | +5 mL Lactic Acid |
| 1:30-3:00 p.m. | Remin: Artificial Saliva Soak |
| 3:00-3:02 p.m. | Fluoride Treatment |
| 3:02-3:30 p.m. | Remin: Artificial Saliva Soak |
| 3:30-3:50 p.m. | Demin: Lactic Acid Challenge (15 mL) |
| 3:50-4:00 p.m. | +Calcium Treatment |
| 4:00-4:10 p.m. | +5 mL Lactic Acid |
| 4:10-4:20 p.m. | +5 mL Lactic Acid |
| 4:20-4:30 p.m. | +5 mL Lactic Acid |
| 4:30 p.m.-9:00 a.m. | Remin: Overnight Artificial Saliva Soak |

During the acid challenge periods (Demin: Lactic Acid Challenge), a 15 ml aliquot of the lesion forming solution was transferred to a treatment beaker containing six enamel specimens. Calcium compounds at equimolar calcium concentration, were introduced to the solution 20 minutes after the start of the acid challenge. The masses of the calcium compounds are shown in Table 3. To simulate clearance of the calcium by saliva, 5 mL of fresh lesion forming solution was added every 10 minutes.

TABLE 3

Mass of powder to be introduced during demineralization periods

| Calcium compound | Mass (mg) |
|---|---|
| Alpha-Tricalcium Phosphate | 25 |
| Calcium Carbonate | 24 |
| Calcium Chloride Dihydrate | 35 |

The pH cycling regimens were repeated for five consecutive days. Two poorly soluble calcium compounds (Alpha-Tricalcium Phosphate and Calcium Carbonate) were compared to one highly soluble calcium compound (Calcium Chloride Dihydrate). As a negative control, the calcium sources, as well as the fluoride source, were replaced with water. Also, for comparison purposes, a study was performed with only the fluoride source.

After five days of treatment and pH cycling, remineralization efficacy was measured from change in surface microhardness (SMH) and enamel fluoride uptake (EFU). The surface microhardness was measured as described above, where the indentations were measured next to the baseline indentations. The fluoride content was determined by microdrilling to a depth of 100 micron into each tooth. The enamel powder from the drill hole was collected, dissolved (20 microliter of $HClO_4$, 40 microliter Citrate/EDTA Buffer and 40 microliter deionized (DI) water) and analyzed for fluoride by comparison to a similarly prepared standard curve. Tables 4 and 5 summarize the results of pH cycling Regimen I and II, respectively.

TABLE 4

Results of 5-Day treatment and pH cycling by regimen I

| | SMH (VHN) | EFU (micro g/cm$^3$) |
|---|---|---|
| Water | 30.1 (1.2) | 151 (19) |
| 100 ppm F | 48.7 (4.4) | 2705 (124) |
| 100 ppm F + aTCP | 85.3 (6.3) | 2726 (135) |
| 100 ppm F + CaCO3 | 93 (3.9) | 2942 (67) |
| 100 ppm F + CaCl2 | 83.4 (6.4) | 2900 (14) |

TABLE 5

Results of 5-Day treatment and pH cycling by regimen II

| | SMH (VHN) | EFU (micro g/cm³) |
|---|---|---|
| Water | 12.6 (1.3) | 80 (5) |
| 100 ppm F | 20.2 (1.9) | 1509 (54) |
| 100 ppm F + aTCP | 27.1 (3.3) | 1696 (138) |
| 100 ppm F + CaCO3 | 22.4 (1.2) | 1737 (99) |
| 100 ppm F + CaCl2 | 57.7 (9.3) | 2352 (190) |

Table 4 shows that after five days of Regimen I treatment and pH cycling, the surface microhardness (SMH) of all calcium treated specimens were significantly higher than that of the negative control (water only) specimens, as well as that of the specimens only treated with 100 ppm F. The SMH of the specimens only treated with 100 ppm F was also significantly higher than that of the negative control (water only). The SMH of the specimens treated with the two poorly soluble calcium compounds (Alpha-Tricalcium Phosphate and Calcium Carbonate) were comparable to the SMH of the highly soluble calcium compound (Calcium Chloride Dihydrate) treated specimens.

The table also shows that after five days of Regimen I treatment and pH cycling, the enamel fluoride uptake (EFU) of all calcium treated specimens were significantly higher than that of the negative control (water only) specimens, and equivalent to the EFU of the specimens only treated with 100 ppm F. The EFU of the specimens only treated with 100 ppm F was significantly higher than that of the negative control (water only) specimens. The EFU of the specimens treated with the two poorly soluble calcium compounds (Alpha-Tricalcium Phosphate and Calcium Carbonate) were comparable to the EFU of the highly soluble calcium compound (Calcium Chloride Dihydrate) treated specimens.

Table 5 shows that after five days of Regimen II treatment and pH cycling, the surface microhardness (SMH) of all calcium treated specimens were significantly higher than that of the negative control (water only) specimens. The SMH of the specimens only treated with 100 ppm F was also significantly higher than that of the negative control (water only) specimens. The SMH of the specimens treated with the two poorly soluble calcium compounds (Alpha-Tricalcium Phosphate and Calcium Carbonate) were comparable to the SMH of the specimens only treated with 100 ppm F. The highly soluble calcium compound (Calcium Chloride Dihydrate) treated specimens had the highest values of SMH.

The table also shows that after five days of Regimen II treatment and pH cycling, the enamel fluoride uptake (EFU) of all calcium treated specimens were significantly higher than that of the negative control (water only) specimens. The EFU of the specimens only treated with 100 ppm F was also significantly higher than that of the negative control (water only) specimens. The EFU of the specimens treated with the two poorly soluble calcium compounds (Alpha-Tricalcium Phosphate and Calcium Carbonate) were equivalent to the EFU of the specimens only treated with 100 ppm F, while the EFU of the highly soluble calcium compound (Calcium Chloride Dihydrate) treated specimens were the highest values of EFU.

Example 2: pH Study

The ability of highly soluble and poorly soluble forms of calcium to influence oral cavity pH was evaluated by the addition of calcium compounds at equimolar calcium concentration (8 mM Ca) to the lesion forming solution described in Example 1. Powders were added and allowed to stir for 30 minutes at 37 degrees C. before measuring the pH. The change in pH following addition of alpha-tricalcium phosphate, calcium carbonate, and calcium chloride are given in Table 6. The insoluble forms of calcium resulted in an increase in pH of the lesion forming solution and the soluble calcium resulted in a drop in pH.

TABLE 6

Change in pH of lesion forming solution following addition calcium compounds

| Calcium compound | ΔpH |
|---|---|
| Alpha-Tricalcium Phosphate | +0.33 |
| Calcium Carbonate | +0.64 |
| Calcium Chloride Dihydrate | −0.14 |

Example 3: Dissolution of Calcium Compounds in Plaque Fluid

Dissolution of calcium compounds in plaque fluid was simulated using multicomponent thermodynamic speciation modelling, implemented using the software Geochemist's Workbench. The initial plaque fluid composition was modeled after starved plaque fluid from caries-free individuals. To simulate the low pH conditions following eating the initial pH was set to pH 5. Precipitation was suppressed for all minerals except for the mineral being modeled.

Figure 1:
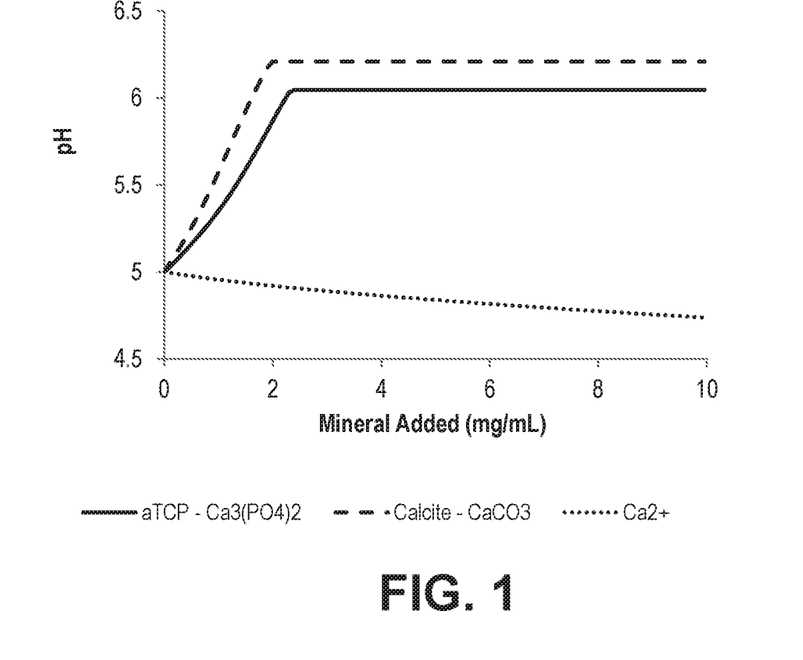
FIG. 1 is a plot of pH versus the amount of mineral added for the highly soluble and poorly soluble forms of calcium generated from the Geochemist's Workbench software model.

FIG. 1 is a plot of pH versus the amount of mineral added for the highly soluble and poorly soluble forms of calcium generated from the software model. The plot shows that addition of alpha-tricalcium phosphate and calcium carbonate to simulated acidic plaque fluid results in an increase in pH from pH 5 to pH 6 or above when saturation is reached. Addition of soluble calcium results in a decrease in pH.

Figure 2:
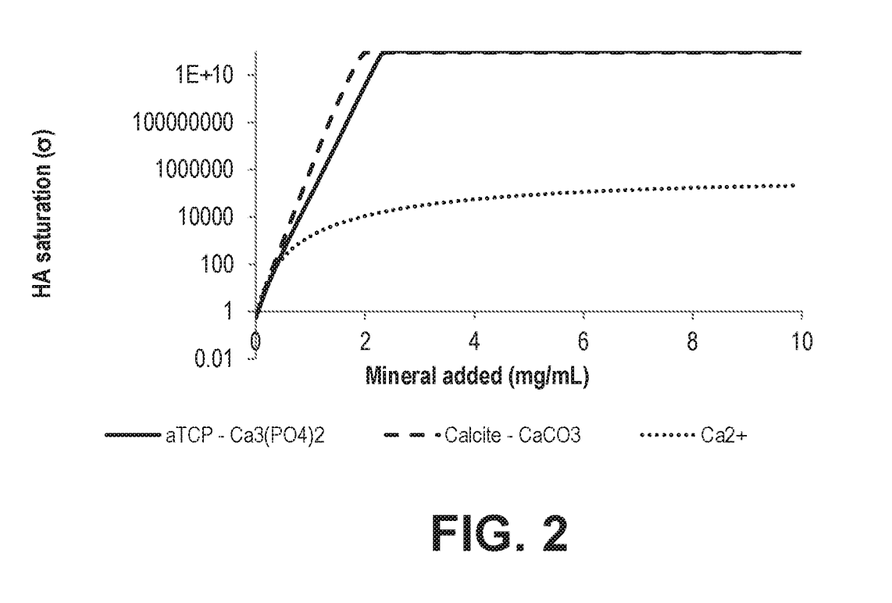
FIG. 2 is a graph of HA saturation level versus the amount of mineral added for the highly soluble and poorly soluble forms of calcium generated from the Geochemist's Workbench software model.

FIG. 2 is a graph of HA saturation level versus the amount of mineral added for the highly soluble and poorly soluble forms of calcium. The plot shows that addition of alpha-tricalcium phosphate or calcium carbonate to simulated acidic plaque fluid results in an increase in hydroxyapatite supersaturation. At the solubility limit of alpha-tricalcium phosphate or calcium carbonate, hydroxyapatite supersaturation is at least five orders of magnitude greater than with addition of soluble calcium.

Example 4: Saliva pH and Buffer Capacity

The impact of calcium carbonate on saliva pH and buffer capacity was measured from saliva collected before and after consumption of a tablet containing 112 mg (7%) of calcium carbonate. Five subjects were asked to chew the tablet for 10 seconds, swish the generated liquid for 40 seconds and then swallow. Saliva was collected for five minutes prior to tablet use, and for five minutes immediately following.

The collected saliva was homogenized by vortexing for 20 seconds and the pH measured using a pH electrode. The buffer capacity, defined as the mM of HCl required to drop the pH by one unit, was determined by acid titration. 0.1 M HCl was added 20-40 uL at a time to 0.5 mL of saliva, and the pH measured after each addition until the pH dropped below pH=5. The buffer capacity was calculated from the slope of the linear regression of mM of HCl added over the change in pH.

TABLE 7

Average saliva pH and buffer capacity before and after
use of a tablet containing calcium carbonate (n = 5).

|  | pH | Buffer Capacity (mM HCl) |
| --- | --- | --- |
| Before tablet use (baseline) | 6.9 (0.2) | 7.4 (0.5) |
| After tablet use | 7.7 (0.1) | 5.5 (0.3) |

What is claimed is:

1. A method of providing a benefit to the oral cavity comprising administering to the oral cavity a poorly-soluble calcium compound and subsequently introducing fluoride to said oral cavity for reacting with the administered calcium to form calcium-bound fluoride deposits in plaque, on teeth and in oral tissue.

2. The method of claim 1 wherein said poorly-soluble calcium compound is administered to the oral cavity within thirty minutes after ingesting food.

3. The method of claim 1 wherein said fluoride is introduced to the oral cavity within twelve hours of administering the poorly-soluble calcium compound.

4. The method of claim 1 wherein said fluoride is introduced to the oral cavity within four hours of administering the poorly-soluble calcium compound.

5. The method of claim 1 wherein said poorly-soluble calcium compound is selected from the group consisting of calcium phosphate, calcium carbonate, calcium oxalate, calcium silicate, and combinations of two or more thereof.

6. The method of claim 1 wherein said poorly-soluble calcium compound comprises calcium carbonate.

7. The method of claim 1 wherein said step of introducing fluoride comprises introducing to the oral cavity a fluoride-containing compound selected from the group consisting of sodium fluoride, sodium monofluorophosphate, stannous fluoride, amine fluorides, titanium tetrafluoride, and combinations of two or more thereof.

8. The method of claim 1 wherein said poorly-soluble calcium compound is administered in the form of a tablet.

9. The method of claim 7 wherein said fluoride-containing compound is introduced in the form of a mouthwash, mouth rinse, or toothpaste.

\* \* \* \* \*